United States Patent [19]

Kubicek

[11] 4,277,623

[45] Jul. 7, 1981

[54] CONVERSION OF ALKANE AND/OR CYCLOALKANE THIOLS TO DISULFIDE WITH CATALYST SYSTEM COMPRISED OF COBALT MOLYBDATE AND AN ALKALI- OR ALKALINE EARTH METAL HYDROXIDE

[75] Inventor: Donald H. Kubicek, Bartlesville, Okla.

[73] Assignee: Phillips Petroleum Company, Bartlesville, Okla.

[21] Appl. No.: 67,645

[22] Filed: Aug. 17, 1979

[51] Int. Cl.$^3$ ............................................. C07C 149/10
[52] U.S. Cl. ..................................................... 568/26
[58] Field of Search ............................ 260/608; 568/26

[56] References Cited

U.S. PATENT DOCUMENTS

| | | | |
|---|---|---|---|
| 2,574,884 | 11/1951 | Mertz et al. | 260/608 |
| 2,966,453 | 12/1960 | Gleim et al. | 208/206 |
| 3,340,324 | 9/1967 | Warner | 260/608 |
| 3,565,959 | 2/1971 | Takase et al. | 260/608 |
| 3,978,137 | 8/1976 | Frame | 260/608 |
| 4,090,954 | 5/1978 | Ward | 260/608 |

FOREIGN PATENT DOCUMENTS 1524592  5/1968  France .................................... 260/608

*Primary Examiner*—Donald G. Daus
*Assistant Examiner*—M. C. Eakin

[57] ABSTRACT

An alkane and/or cycloalkane thiol is converted to disulfide with oxygen or air in presence of a catalyst system comprising a cobalt molybdate-alkali metal- and/or an alkaline earth metal hydroxide. A solvent, e.g., an alcohol or an alcohol-water mixture is employed. In one embodiment, 2-methyl-2-propane thiol (tertiary-butyl mercaptan) is converted.

7 Claims, No Drawings

CONVERSION OF ALKANE AND/OR CYCLOALKANE THIOLS TO DISULFIDE WITH CATALYST SYSTEM COMPRISED OF COBALT MOLYBDATE AND AN ALKALI- OR ALKALINE EARTH METAL HYDROXIDE

BRIEF SUMMARY OF THE INVENTION

An alkane and/or cycloalkane thiol is converted to a corresponding disulfide in presence of oxygen or air and with a catalyst system essentially comprising a cobalt molybdate-alkali metal- and/or an alkaline earth metal hydroxide. An alcohol or an alcohol-water mixture is employed as solvent.

DETAILED DESCRIPTION

This invention relates to a process for the conversion of an alkane and/or a cyloalkane thiol to a disulfide e.g. to the corresponding disulfide. In another of its aspects the invention relates to the provision of a catalyst system or combination especially suited to the conversion of an alkane and/or a cycloalkane thiol to a corresponding disulfide. In a further aspect of the invention it relates to the oxidation of an alkane and/or a cycloalkane thiol to its corresponding disulfide.

In one of its concepts the invention provides a process for the conversion of at least one of an alkane thiol and a cycloalkane thiol to a disulfide by subjecting the same to oxidation, as with air or oxygen, in the presence of a catalyst essentially comprising a supported cobalt molybdate and at least one of an alkali metal- and alkaline earth metal hydroxide. In another of its concepts the invention provides a process as herein described wherein the thiol, catalyst system and solvent are simply placed into a closed reactor under a suitable pressure of air and wherein air is passed through the reactor in which heat is generated by the ensuing reaction. In a further concept, a temperature of the reaction, which has been allowed to rise, is maintained at a desired level as by cooling.

Organic disulfides have varied applications ranging from intermediates for insecticides, herbicides and rodent repellents to additives in greases and diesel fuels. The synthesis of such disulfides is well known. These are generally prepared from the corresponding thiols (mercaptans).

U.S. Pat. No. 3,994,979 describes conversion of 2-methyl-2-propanethiol (tert-butyl mercaptan) to di-tert-butyl disulfide using sodium hydroxide, elemental sulfur and N-methylpyrrolidone solvent. This is a two-step process in which a mercaptide is formed first. In the second step the sulfur oxidizes the mercaptide to the disulfide.

U.S. Pat. No. 3,340,324 describes preparation of di-tert-butyl disulfide from 2-methyl-2-propanethiol and elemental sulfur in the presence of an alcohol and an alkali metal hydroxide. No air or oxygen appears to be present in the reaction zone, further, the data show the use of large proportions of sodium hydroxide are needed to produce good yields of disulfide.

U.S. Pat. No. 2,574,884 describes the oxidation of tertiary alkanethiols to di-tertiary alkyl disulfides in the presence of oxygen using alumina-based catalysts like chromia, vanadia and iron oxide.

Each of the above references and others have a common disadvantage, namely a low thiol conversion and/or a low disulfide selectivity.

It would be of economic and chemical importance to combine certain features of some of the disulfide preparations which are known into a process wherein disulfides are prepared in a one-step process in near quantitative selectivity and thiol conversion. The present invention provides such a process.

It is an object of this invention to convert an alkane and/or a cycloalkane thiol to a corresponding disulfide. It is another object of this invention to provide a catalyst system or combination suited to provide near quantitative selectivity and conversion of an alkane and/or cycloalkane thiol to a corresponding disulfide. It is a further object of the invention to provide a process yielding a high thiol conversion and a high selectivity to the formation of the corresponding disulfide e.g. for the conversion of tertiary butyl mercaptan to di-tertiary-butyl disulfide.

Other aspects, concepts, objects, and the several advantages of the invention are apparent from a study of this disclosure and the appended claims.

According to the present invention there is provided a process for the conversion of at least one of an alkane thiol and a cycloalkane thiol to a disulfide which comprises subjecting said alkane to oxidation as with air or oxygen, in the presence of a catalyst system or combination essentially comprising a supported cobalt molybdate and at least one of an alkali metal and alkaline earth metal hydroxide.

As evident from the data herein, the one-step process of the invention is operative to yield high conversion and selectivity with various mercaptans using only a small amount or proportion of alkali metal or alkaline earth metal hydroxide. For example, viewing the high yield of thiol conversion and selectivity to formation of disulfide there is noted, as earlier stated, a considerably reduced proportion of hydroxide to be needed in the process of the invention.

Thiols useful in this invention are those materials which are represented by the formula

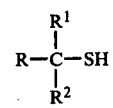

wherein R, $R^1$, $R^2$ can be hydrogen or an alkyl or cycloalkyl radical ranging from 1 to 20 carbon atoms wherein R and $R^1$ taken together can be an alkylene radical having from 5 to 10 carbon atoms. For example, materials to be used that correspond to the above formula can be, but are not limited to:

methanethiol
ethanethiol
1-propanethiol
2-propanethiol
1-butanethiol
2-butanethiol
2-methyl-2-propanethiol (tert-butyl mercaptan)
1-pentanethiol
2-pentanethiol
3-pentanethiol
2-methyl-2-butanethiol
3-methyl-2-pentanethiol
1-hexanethiol
2-hexanethiol
3-hexanethiol
2-methyl-2-pentanethiol cyclohexanethiol
4-methylcyclohexanethiol
1-methylcyclohexanethiol
and the like and mixtures thereof.

The catalyst useful in this invention is comprised of at least one of an alkali or alkaline earth metal hydroxide with a supported suitable cobalt molybdate co-catalyst. Any suitable supported cobalt molybdate catalyst is within the scope of this invention and the appended claims. The supported catalyst is especially useful with mercaptans that are difficult to convert to the disulfide, e.g., tertiary alkyl mercaptan. The specific cobalt molybdate catalyst employed in the current invention was HDS-2 (a hydrodesulfurization catalyst) from American Cyanamid Co. The composition of this catalyst is listed below.

| HDS-2 (American Cyanamid) | |
| --- | --- |
| Ingredient | Wt. % |
| Cobalt Oxide | 3-4 |
| Molybdenum Oxide | 15-16 |
| Sodium Oxide | 0.4 |
| Iron Oxide | 0.05 |
| Alumina (support) | Balance |

Although the catalyst support employed herein was alumina other suitable supports which are chemically inert or do not adversely affect the reaction are considered within the scope of this invention. Such supports might be in addition to alumina, silica-alumina, magnesium oxide, charcoal, silica, silica-carbide and the like.

The alkali metal hydroxides are preferred as co-catalysts in the catalyst system of the invention when both a hydroxide and the cobalt-containing catalyst are employed. Examples of such materials are lithium hydroxide, sodium hydroxide, potassium hydroxide, rubidium hydroxide and cesium hydroxide. Alkaline earth metal hydroxides can also be employed but are less preferred. Examples of such materials are those hydroxides of the metals in Group IIA of the Periodic Table of Elements. The alkali or alkaline earth metal hydroxide can be in the form of a powder, pellet or as an aqueous solution, preferably no more dilute than 50 wt. %.

The amount of alkali or alkaline earth metal hydroxide used relative to the supported cobalt molybdate can be varied depending upon desired reaction conditions, etc. Generally, the weight range of catalyst per mole of thiol is considered to be

| | Wt. Range, grams | |
| --- | --- | --- |
| | Broad | Preferred |
| Cobalt Molybdate on Support | .02-.06 | 0.1-0.4 |
| Alkali and/or Alkaline Earth Metal Hydroxide | 0.2-4.0 | 1.50-3.0 |

The amount of thiol used relative to the above catalyst and co-catalyst weight ranges in Example I is about 1.0 mole of thiol to about 2.4 grams of catalyst/co-catalyst.

Depending upon the alkali metal in the hydroxide used the proportion of the hydroxide present will range, broadly, from about 0.001 to about 0.2 moles per mole of mercaptan. For example, in the case of NaOH, now preferred because of cost, etc., the range is for about 0.025 to about 0.08 moles per mol of mercaptan. This is in sharp contrast with the use of very much lower amounts of alkali metal hydroxide in the art above noted.

Air or oxygen can be used in the current invention. When air or oxygen is bubbled through the reaction mixture, the rate of air or oxygen passage preferably should be fast but not so fast that the flow will remove reactant. If the gas is not bubbled through but only reacted within a sealed system it is preferred to have a nitrogen blanket and to add oxygen as it is absorbed. This will avoid explosive mixtures from forming. The rate of air or oxygen flow through the system can be determined by routine testing. A flow, arbitrarily selected at 2-4 scf (standard cubic feet)/hour is now preferred.

Alcohols are preferred solvents in this invention. Any alcohol in which the thiol reactant is at least partially soluble is satisfactory as a solvent. It is now preferred that the alkali or alkaline earth metal hydroxide have some solubility in the alcohol. Alcohol-water mixtures (e.g. 90 wt. % alcohol-10% water) can also be employed. Alcohols having 1 to 10 carbon atoms can be used. Examples of some suitable alcohols are methyl alcohol, ethyl alcohol, propyl alcohol, isopropyl alcohol, butyl alcohol, decyl alcohol and the like and mixtures thereof.

Conditions employed in the current invention are shown as follows:

| | | Broad | Preferred |
| --- | --- | --- | --- |
| Temperature: | °F. | 60-350 | 70-250 |
| | °C. | 15.6-176.7 | 21.1-121.1 |
| Pressure: | psig | 10-1000 | 25-500 |
| | MPa | 0.069-6.895 | 0.172-3.447 |

The following examples serve to illustrate the operability of the current invention.

EXAMPLE 1

This is an inventive run illustrating the current invention. To a 1 gallon 316 stainless steel autoclave equipped with a stirrer, internal cooling coils, overhead condenser, back pressure regulator and air addition tube was charged 2 grams of cobalt molybdate on alumina catalyst (HDS-2), 10 grams solid sodium hydroxide pellets, 250 milliliters (198 grams) methyl alcohol, and 500 milliliters (403 grams, 4.97 moles) of 2-methyl-2-propanethiol (tertiary-butyl mercaptan). After closing the reactor, the agitator was started and the system pressured to 300 psig (2.068 MPa) with air at about 25° C. (77° F.). An air flow was then started through the reaction mixture (e.g. below the liquid surface) at such a rate that a minimum amount of alcohol and mercaptan were carried overhead through the condenser (2.5 cubic feet/hr.). The reactor temperature was allowed to rise to about 54°-60° C. (130°-140° F.) due to the heat generated by the reaction. This temperature was then maintained by the addition of cooling water through the coils. After 4 hrs., the reaction mixture was cooled to about 25° C. vented and transferred to a separatory funnel. Two liquid phases formed. Each of these phases was analyzed by GLC using a 12 ft. column packed with 10% SE 30 silicon rubber on 60-80 mesh Chromosorb P that had been previously mineral acid washed and dried. The top phase (212 grams) contained 94.3 wt. % methyl alcohol, 0.2 wt. % 2-methyl-2-propanethiol, 5.0 wt. % di-tert-butyl disulfide, and 0.5 wt. % heavies. The bottom phase (395 grams) contained 9.3 wt. % methyl alcohol, a trace of 2-methyl-2-propanethiol, 90.6 wt. % di-tert-butyl disulfide and 1.1 wt. % heavies. Based on these analyses there was obtained a 99 wt. % conversion of 2-methyl-2-propanethiol with an 85 wt. % selectivity of di-tert-butyl disulfide. The top phase was stripped at atmospheric pressure to 81° C. (187° F.) head temperature, 115° C. (239° F.) kettle temperature to remove the alcohol and the kettle product combined with the bottom phase and fractionated at 100 mm vacuum. An 84 wt. % distilled yield of di-tert-butyl disulfide was obtained distilling mostly at 125° C. (257° F.)/100 mm.

EXAMPLE II

This is an inventive run similar to Example I except the 10 grams of sodium hydroxide employed was pre-dissolved in 10 milliliters of water. Although this facilitated the ease of handling, the di-tert-butyl disulfide product selectivity dropped from 85 wt. % to 80 wt. %, the thiol conversion remaining at 99 wt. %.

EXAMPLE III

This example is an inventive run similar to Example I except isopropyl alcohol was used in place of methyl alcohol. Analysis after the reaction was complete showed a 96 wt. % conversion of 2-methyl-2-propanethiol with an 89 wt. % selectivity to di-tert-butyl disulfide. Although the use of isopropyl alcohol appears to be equal to methyl alcohol in conversion and product selectivity, the degree of solubility is different. The di-tert-butyl disulfide product is more soluble in isopropyl alcohol than methyl alcohol which makes separation slightly more difficult. Table I illustrates the differences in these solubilities.

TABLE I
Reaction Mixture Solubilities

| | Analysis by GLC, Wt. % | | | |
|---|---|---|---|---|
| | Methyl Alcohol | | Isopropyl Alcohol | |
| Composition | Top Phase | Bottom Phase | Top Phase | Bottom Phase |
| Alcohol | 94.3 | 8.3 | 37.8 | 64.6 |
| 2-Methyl-2-propanethiol | 0.2 | trace | — | 17.4 |
| Di-tert-butyl disulfide | 5.0 | 90.6 | 58.9 | 16.2 |
| Heavies | 0.5 | 1.1 | 3.3 | 1.8 |

EXAMPLE IV

This is an inventive run similar to Example I except it was run under batch conditions and at a higher temperature. To a stirred 300 milliliter 316 stainless steel autoclave was charged 0.2 grams HDS-2 catalyst, 1.0 grams solid sodium hydroxide, 25 milliliters methyl alcohol and 50 milliliters (40.3 grams, 0.49 moles) of 2-methyl-2-propanethiol. The reactor was pressured with air to 300 psig (2.068 MPa) and the contents heated to 162° C. (325° F.). The pressure at this point was 520 psig (3.585 MPa). After 15 mins. stirring, the contents were cooled to about 21° C. (70° F.). The pressure was released to 0 psig and re-pressured with air to 300 psig (2.068 Mpa). The contents were again stirred and heated to 162° C. (325° F.). After 15 mins. at 162° C./520 psig the contents were again cooled to 21° C. (70° F.) and the reactor vented. The heating and pressuring procedure was repeated for a third time. After cooling and venting, there was obtained 2 phases which were separated and analyzed as described in Example I. The top phase, 28 milliliters, contained 93.1 wt. % methyl alcohol, 1.2 wt. % 2-methyl-2-propanethiol, 5.2 wt. % di-tert-butyl disulfide and 0.5 wt. % heavies. The bottom phase contained 1.8 wt. % methyl alcohol, 0.1 wt. % 2-methyl-2-propanethiol 99.4 wt. % di-tert-butyl disulfide and 0.7 wt. % heavies. Based on these analysis there was obtained at 98 wt. % of 2-methyl-2-propanethiol conversion with a 97 wt. % selectivity to di-tert-butyl disulfide.

EXAMPLE V

This example illustrates the disadvantages of using too much sodium hydroxide and water in the reaction system. The procedure described in Example IV was repeated except the amount of sodium hydroxide employed was increased. These results are shown in Table II. Run No. 1 is the inventive run described in Example I. The reaction temperatures are higher for runs 2, 3, and 4 but the temperature is not a significant factor in product selectivity (Refer Example IV). The data in Table II shows that increasing the amount of sodium hydroxide (gms. NaOH per ml of thiol) is detrimental to product selectivity, although thiol conversion is generally above 90%. The data from Run 4 also shows the need for the cobalt molybdate on alumina catalyst component when converting tertiary butyl mercaptan. Without it the product selectivity is greatly reduced.

TABLE II
Effect of Sodium Hydroxide Concentration On Conversion of Tert-Butyl Mercaptan to Di-tert-Butyl Disulfide

| | Ingredients | | | | | Reaction | % Thiol | % Selectivity |
|---|---|---|---|---|---|---|---|---|
| Run No. | t-C₄SH, ml | MeOH, ml | Water, ml | NaOH, g | HDS-2, g | Temp, °C. | Conversion | Di-tert-Butyl Disulfide |
| 1 | 500 | 250 | 10 | 10 | 2.0 | 25-60 | 99 | 85 |
| 2 | 50 | — | 100 | 12.5 | 0.25 | 21-162 | 90 | 57 |
| 3 | 50 | — | 100 | 25.0 | 0.25 | 21-162 | 95 | 25 |
| 4 | 50 | — | 100 | 25.0 | — | 21-162 | 83 | 14 |

EXAMPLE VI

This example is a control run in which it is shown that conversion and product selectivity is greatly reduced when sodium hydroxide is omitted from the HDS-2 catalyst. The batch operation described in Example IV was essentially repeated using more HDS-2 catalyst but no sodium hydroxide. The charge was 10 grams HDS-2 catalyst, 50 milliliters methyl alcohol and 50 milliliters (40.3 grams, 0.49 moles) of 2-methyl-2-propanethiol. The results in Table III illustrate the necessity of adding an alkali metal hydroxide to the catalyst system. Without sodium hydroxide, more heavies are formed.

TABLE III

Effect of Sodium Hydroxide on Product Distribution

|  | Without Sodium Hydroxide | | With Sodium Hydroxide | |
|---|---|---|---|---|
|  | Top Phase | Bottom Phase | Top Phase | Bottom Phase |
| A. Products, Wt. % by GLC | | | | |
| 1. Methyl Alcohol | 80.5 | 11.0 | 93.1 | 1.8 |
| 2. 2-Methyl-2-propanethiol | 4.0 | 10.2 | 1.2 | 0.1 |
| 3. Di-tert-Butyl Disulfide | 8.1 | 50.0 | 5.2 | 99.4 |
| 4. Heavies | 7.4 | 28.8 | 0.5 | 0.7 |
| B. Conversion of 2-Methyl-2-propanethiol | 84 | | 98 | |
| C. % Selectivity of di-tert-butyl disulfide | 63 | | 97 | |

EXAMPLE VII

This example shows the inventive catalyst composition works equally well with primary and secondary thiols but may not necessarily be needed particularly with primary thiols such as methanethiol. The data listed in Table IV shows good product selectivity and thiol conversion with both 2-propanethiol ($iC_3H_7SH$) and methanethiol ($CH_3SH$) when the cobalt molybdatesodium hydroxide combination is employed. However, with methanethiol it appears the cobalt molybdate catalyst is not needed.

TABLE IV

Conversion of Primary and Secondary Thiols to Disulfide Using Cobalt Molybdate on Alumina-Sodium Hydroxide Catalyst (Reaction Temp. 21–58° C.)

| Run No. | Ingredients | | | | % Thiol Conversion | % Disulfide Selectivity |
|---|---|---|---|---|---|---|
|  | RSH | MeOH, ml | NaOH g | HDS-2, g | | |
| 1 | $CH_3SH$, 59 g (1.22 moles) | 25 | (0.25 mole) | — | 98.5 | 99.8 |
| 2 | $CH_3SH$, 645 g (13.43 moles) | 340 | (0.325 mole) | 2.6 | 94.5 | 100.0 |
| 3 | i-$C_3H_7SH$, 50 ml, 40.3 g (0.49 moles) | 25[a] | (0.25 mole) | 0.2 | 99.0 | 96.0 |

[a]Isopropyl alcohol

Table IV shows that the catalyst system of this invention yields high conversion and selectivity with primary and secondary mercaptans. This result is obtained with a small amount or proportion of NaOH, about 0.025 mol.

The data herein disclosed can be summarized as follows:

1. Primary, secondary and tertiary alkanethiols can be readily converted to the corresponding disulfides when treated at 25° C. to 162° C. with a catalyst comprised of cobalt molybdate on alumina and sodium hydroxide in the presence of an alcohol or water, or alcohol-water mixture. The thiol conversion and disulfide selectivity is near quantitative.

2. The cobalt molybdate on alumina-sodium hydroxide catalyst is particularly effective in converting tertiary alkanethiol to di-tert-alkyl disulfides.

Reasonable variation and modification are possible within the scope of the foregoing description and the appended claims to the invention the essence of which is that there has been set forth a process for the conversion of a mercaptan in high yield and high selectivity to a corresponding disulfide by subjecting the same to the action of oxygen and/or air in presence of a catalyst comprising a relatively small amount of at least one of an alkali metal hydroxide and an alkaline earth metal hydroxide and a cobalt molybdate catalyst, as described; especially in the case of a tertiary mercaptan, e.g., tertiary butyl mercaptan, the catalyst system or combination of the invention employed as described under conditions as described results in highly satisfactory conversions and selectivities to form the corresponding disulfide.

I claim:

1. A process for the conversion of at least one of an alkane and a cycloalkane thiol to a corresponding disulfide in high yield and selectivity which consists essentially of subjecting the same to at least one of oxygen and air in the presence of a catalyst consisting essentially of a small amount of the order of 0.2 to 4 grams per mole of thiol of at least one of an alkali metal hydroxide and alkaline earth metal hydroxide together with a cobalt molybdate catalyst, the cobalt molybdate catalyst being on a suitable support and being substantially insoluble in the reaction medium, and the reaction being effected with the aid of a solvent which is at least one comprised of an alcohol in which the hydroxide is soluble and said alcohol and water.

2. A process according to claim 1 wherein said support is at least one of alumina, silica-alumina, magnesium oxide, charcoal, silica, and silica-carbide.

3. A process according to claim 1 wherein the support is alumina.

4. A process according to claim 1 wherein the mercaptan is a tertiary thiol.

5. A process according to claim 4 wherein the tertiary thiol is 2-methyl-2-propanethiol.

6. A process according to claim 5 wherein both alcohol and water are present.

7. A process according to claim 1 wherein the thiol is represented by the formula

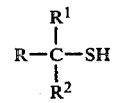

wherein R, $R^1$, $R^2$ can be hydrogen or an alkyl or cycloalkyl radical ranging from 1 to 20 carbon atoms and wherein R and $R^1$ taken together can be an alkylene radical having from 5 to 10 carbon atoms.

* * * * *